United States Patent
Douglas et al.

[11] Patent Number: 5,843,691
[45] Date of Patent: Dec. 1, 1998

[54] VISUALLY-READABLE REAGENT TEST STRIP

[75] Inventors: Joel Douglas, Santa Clara; Ernest Kiser, Los Altos; Michael F. Tomasco, Cupertino; Remedios Dato, Pleasanton; Edward G. Rice, Palo Alto; Deborah P. Tuohy, Cupertino; Mark Maxson; Zbigniew Witko, both of San Jose; Scott Segelke, Mountain View, all of Calif.

[73] Assignee: Lifescan, Inc., Milpitas, Calif.

[21] Appl. No.: 779,735

[22] Filed: Dec. 31, 1996

(Under 37 CFR 1.47)

Related U.S. Application Data

[63] Continuation-in-part of Ser. No. 743,432, Nov. 1, 1996, which is a continuation of Ser. No. 528,511, Aug. 3, 1995, abandoned, which is a continuation-in-part of Ser. No. 411,238, Mar. 27, 1995, abandoned, and Ser. No. 442,035, May 15, 1993, abandoned.

[51] Int. Cl.⁶ .............. C12Q 1/54; C12Q 1/28; G01N 21/00
[52] U.S. Cl. .............. 435/14; 435/28; 422/55; 436/170
[58] Field of Search ........... 435/14, 28; 422/55–58; 436/166, 169, 170

[56] References Cited

U.S. PATENT DOCUMENTS

| | | | |
|---|---|---|---|
| 3,552,928 | 1/1971 | Fetter | 23/253 |
| 3,964,871 | 6/1976 | Hochstrasser | 23/253 |
| 4,683,209 | 7/1987 | Ismeil et al. | 436/14 |
| 4,738,823 | 4/1988 | Engelmann | 422/56 |
| 4,810,470 | 3/1989 | Burkhardt et al. | 422/56 |
| 4,994,238 | 2/1991 | Daffern et al. | 422/56 |
| 5,032,506 | 7/1991 | Palmer et al. | 435/26 |
| 5,036,000 | 7/1991 | Palmer et al. | 435/26 |
| 5,156,954 | 10/1992 | Mielke et al. | 435/18 |
| 5,208,163 | 5/1993 | Charlton et al. | 436/63 |
| 5,306,623 | 4/1994 | Kiser et al. | 435/14 |
| 5,478,751 | 12/1995 | Oosta et al. | 436/165 |
| 5,563,042 | 10/1996 | Phillips et al. | 435/14 |
| 5,607,565 | 3/1997 | Azarnia et al. | 204/403 |
| 5,719,034 | 2/1998 | Kiser et al. | 435/14 |

FOREIGN PATENT DOCUMENTS

| | | | |
|---|---|---|---|
| 0 317 070 A2 | 5/1989 | European Pat. Off. | C12Q 1/28 |
| 0 475 692 A1 | 3/1992 | European Pat. Off. | G01N 33/52 |
| 0 735 369 A1 | 10/1996 | European Pat. Off. | G01N 33/52 |
| 0 759 555 A2 | 2/1997 | European Pat. Off. | G01N 33/52 |
| 0 769 558 A1 | 4/1997 | European Pat. Off. | C12Q 1/54 |
| 0 826 777 A1 | 3/1998 | European Pat. Off. | C12Q 1/54 |
| 2 090 659 | 7/1982 | United Kingdom | G01N 33/48 |
| WO 85/01747 | 4/1985 | WIPO | C12Q 1/00 |
| WO 96/32635 | 10/1996 | WIPO . | |

*Primary Examiner*—Ralph Gitomer
*Attorney, Agent, or Firm*—James Riesenfeld

[57] ABSTRACT

A multilayer reagent test strip measures the concentration of analyte in a liquid sample that is applied to it. The sample is guided to a number of assay areas arrayed along the strip, where the analyte can react with a reagent to cause a color change. Each assay area also includes an inhibitor for the color-change reaction. The inhibitor concentration increases in successive assay areas; thus, the number of areas that change color is a measure of the analyte concentration. The test strip is particularly adapted for measuring glucose in a whole blood sample. In a preferred embodiment, the sample is guided to the assay areas along a path formed by crushing selected areas of a membrane, and the assay areas are uncrushed areas of the membrane.

31 Claims, 10 Drawing Sheets

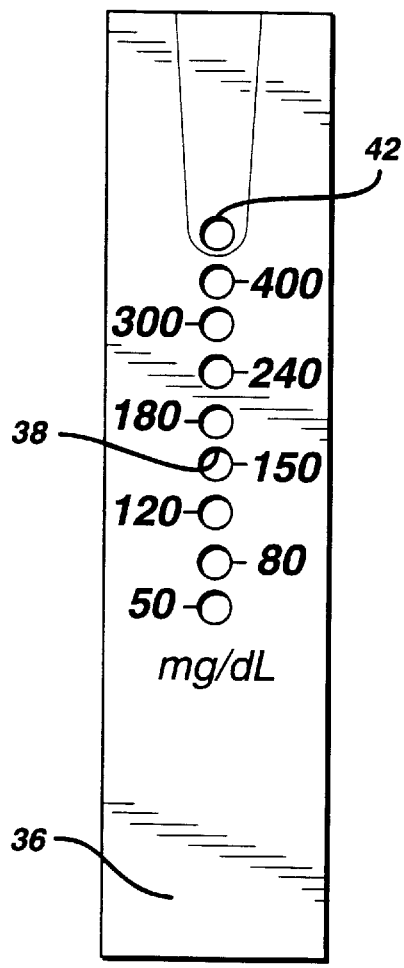
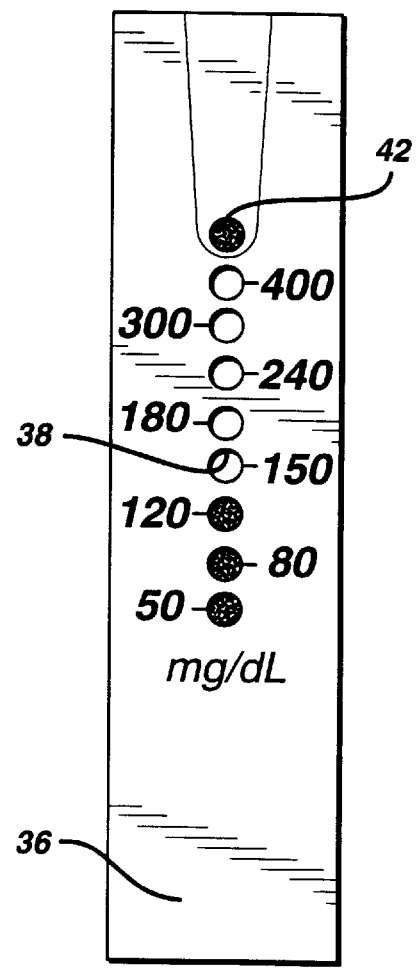

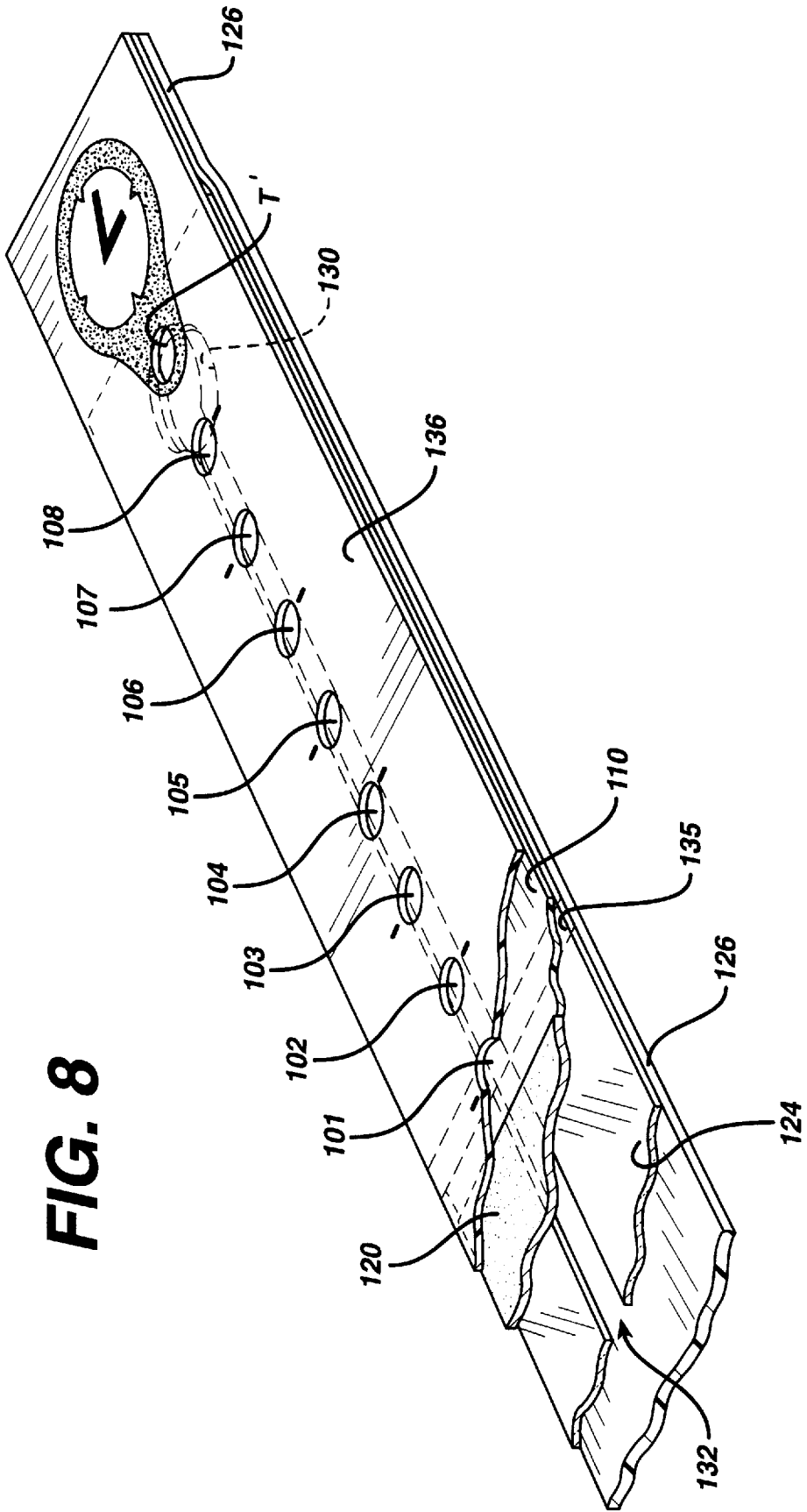

VISUALLY-READABLE REAGENT TEST STRIP

CROSS-REFERENCE TO RELATED APPLICATION

This application is a continuation-in-part of copending U.S. application Ser. No. 08/743,432, filed Nov. 1, 1996, now pending which is a continuation of Ser. No. 528,511, filed Aug. 3, 1995, abandoned, which is a continuation-in-part of Ser. No. 411,238, filed Mar. 27, 1995 now abandoned and Ser. No. 442,035, filed May 15, 1995 now pending.

BACKGROUND OF THE INVENTION

1. Field of the Invention

This invention relates to a dry test strip for measuring the concentration of an analyte in a biological fluid; more particularly, a test strip that measures the concentration directly, without the need for a meter.

2. Description of the Related Art

Many visual test devices have been developed for measuring the concentration of certain analytes in biological fluids. These devices have, for example, measured glucose, cholesterol, proteins, ketones, phenylalanine, or enzymes in blood, urine, or saliva.

Dry phase reagent strips incorporating enzyme-based compositions are used extensively in clinical laboratories, physician's offices, hospitals, and homes to test samples of biological fluids for glucose concentration. In fact, reagent strips have become an everyday necessity for many of the nation's several million diabetics. Since diabetes can cause dangerous anomalies in blood chemistry, it can contribute to vision loss, kidney failure, and other serious medical consequences. To minimize the risk of these consequences, most diabetics must test themselves periodically, then adjust their glucose concentration accordingly, for instance, through diet control and/or with insulin injections. Some patients must test their blood glucose concentration as often as four times daily or more.

It is especially important for diabetics who must control their diet in order to regulate sugar intake and/or administer insulin injections, and who must be guided in this regard by frequent tests of blood glucose concentration, to have rapid, inexpensive, and accurate reagent strips for glucose determination.

Reagent strips are known that contain an indicator which turns a different shade of color, depending on the concentration of glucose in a biological fluid that has been applied to the strip. Although some of these strips use reduction chemistries, more commonly they involve an oxidizable dye or dye couple. Some of the strips include an enzyme, such as glucose oxidase, which is capable of oxidizing glucose to gluconic acid and hydrogen peroxide. They also contain an oxidizable dye and a substance having peroxidative activity, which is capable of selectively catalyzing oxidation of the oxidizable dye in the presence of hydrogen peroxide. (See, for example, U.S. Pat. No. 5,306,623, issued Apr. 26, 1994, to Kiser et al.)

U.S. Pat. No. 3,964,871, issued Jun. 22, 1976, to Hochstrasser, discloses a disposable indicator strip for directly measuring substances, such as glucose, in biological fluids. The indicator registers the concentration of the substance by including both an indicator reagent, which is oxidized and changes color when it reacts with the substance, and an "antagonist" that in some way prevents the accumulation of oxidized indicator until it has been completely consumed.

Palmer et al. disclose a "digital" quantitative assay system for glucose and other analytes in European Patent Application Publication No. 0 317 070, published May 24, 1989 (see also U.S. Pat. No. 5,036,000, issued Jul. 30,1991). That system measures the concentration of an organic compound in a biological fluid by first oxidizing the compound with a substrate-specific oxidase enzyme to produce hydrogen peroxide. The system includes a chromogen that is a reductant of hydrogen peroxide and an air-stable hydrogen peroxide reductant that has a larger reduction potential. The larger reduction potential delays any detectable color change by the chromogen until the air-stable first hydrogen peroxide reductant has been consumed. Thus no color change results if the hydrogen peroxide to be measured is less than a pre-determined level corresponding to the concentration of the air-stable peroxide reductant. As a result, the system measures the concentration quantitatively, independent of color change intensity.

Englemann, U.S. Pat. No. 4,738,823, issued Apr. 19, 1988, discloses a test strip for analyte determination that has a support member, which has an absorbent material positioned to remove excess sample applied to the strip. The strip may also include a cover, which includes an opening through which sample may be introduced.

Burkhardt et al., U.S. Pat. No. 4,810,470, issued Mar. 7, 1989, disclose a device for measuring analyte concentrations in liquid samples. The device includes one or more bibulous matrices covered by a liquid impervious coating or film. The sample is deposited on a portion of a bibulous matrix and is metered into the matrix chromatographically. By wicking action, the sample travels to an assay region that contains a test reagent for the analyte.

Daffern et al., U.S. Pat. No. 4,994,238, issued Feb. 19, 1991, disclose a chemical analysis test device that comprises an absorbent layer, a waterproof barrier layer, and a reagent layer that has a determinate volume. The sample is applied to the reagent layer through aligned holes in the overlying absorbent and barrier layers.

Whether the test is conducted in the home, physician's office, clinic or a hospital, accuracy and reproducibility of a glucose determination are extremely important. In the case of a color-indicating reagent strip, it is desirable that the color change be pronounced and insensitive to variations in components of the biological fluid other than glucose. In the case of a visually-read reagent strip, it is especially important that diabetics, who may have impaired vision, have a strip that exhibits a significant color change dependent upon glucose concentration, although color change as exhibited by a change in absorbance at a given wavelength is also important for the accuracy of meter-read strips.

Since the color change involves a series of chemical reactions, it doesn't happen instantaneously. Thus, the user must wait a period of time—typically a minute or less—for the reactions to take place. When a meter reads the strip, timer circuitry can give a signal that indicates the reactions are completed. However, when a strip is read visually, without a meter, the user may underestimate the time needed, read the strip prematurely, and get an incorrect result. Alternatively, the user may feel the need to wait an excessive time before reading the strip, to be sure the reaction is complete, causing unnecessary delay and user dissatisfaction. There is thus a need for a "chemical" timer; i.e., an element on the strip that will change color regardless of the concentration of glucose (or other analyte of interest) in the sample, but will do so only after sufficient time has passed to complete the color-forming reactions with the sample.

SUMMARY OF THE INVENTION

In accordance with the present invention, an elongated multilayer reagent test strip for measuring the concentration of analyte in a sample of biological fluid that is applied to the strip comprises a) a bottom layer with a through hole for accepting the sample;

b) a membrane layer, having a sample side facing the bottom layer and a testing side opposite to it, and having arrayed along its length a plurality of discrete bibulous assay areas, separated by a non-bibulous region, the membrane containing a reagent that can react with the analyte to produce a color change, the reagent comprising
  i) a first component that interacts with the analyte to form hydrogen peroxide;
  ii) a second component that interacts with the hydrogen peroxide to undergo a color change; and
  iii) a third component that inhibits the change in color of the second component;

c) an intermediate layer between the bottom and membrane layers; and d) metering means for distributing sample along the strip, the metering means comprising a fluid transport channel formed in the intermediate layer for guiding sample over the membrane surface to the bibulous assay areas; the inhibitor concentration increasing in a predetermined way with distance from a first end of the strip, so that a correspondingly increasing analyte concentration must be contained in a sample if it is to effect a color change, whereby one or more assay areas may change color when a sample is applied to the strip, and the color-changing area most distant from the first end indicates the analyte concentration in the sample.

In operation, a method for measuring the concentration of analyte in a sample of biological fluid, comprises the steps of:

(a) applying the sample to a reagent test strip that comprises:
  (i) a bottom layer with a through hole for accepting the sample,
  (ii) a membrane layer, having a sample side facing the bottom layer and comprising a plurality of bibulous assay areas that each change color when contacted with fluid containing at least a predetermined amount of analyte, greater than the amount of analyte that causes a change in color of the assay areas that are closer to a first end of the strip and
  (iii) metering means for distributing the sample from the through hole along a predetermined non-bibulous path to each of the assay areas and (b) determining the analyte concentration by observing the assay area that changes color and that is most distant from the first end of the strip.

The strip is of the type that provides a visible indication of the concentration of an analyte that is contained in a biological fluid applied to a "sample side" of the strip. The visible indication appears on the opposite (or "testing") side of the strip.

The chemical composition of the test strip depends, of course, on the analyte/biological fluid to be measured. Test strips can be designed to detect analytes such as glucose or other sugars, alcohol, cholesterol, proteins, ketones, uric acid, phenylalanine, or enzymes in biological fluids such as blood, urine, and saliva, as well as water. For the sake of convenience and brevity, the reagent test strips disclosed in the most detail in this specification detect glucose in blood. A person of ordinary skill in the art could readily adapt the information in this disclosure for detecting other analyte/biological fluid combinations.

A test strip of the present invention provides a relatively simple and rapid determination of glucose concentration in an unmeasured sample of blood. The strip comprises a bottom layer with a hole through which a sample may be introduced to the sample side of a porous matrix, whose opposite side is the testing side. The matrix is generally a membrane and the two terms are used interchangeably in the present specification and the appended claims. A testing reagent is applied to the matrix and, to a greater or lesser extent, is impregnated within the pores of the matrix. For simplicity, we sometimes refer to the reagent on the matrix as a "coating", in this specification and in the appended claims, recognizing that the reagent coating penetrates the matrix.

An intermediate layer lies between the bottom layer and the matrix. In one embodiment, cutouts in the intermediate layer align with non-bibulous areas of the membrane to guide the sample to a series of bibulous assay areas that are arrayed along the strip. (As used in this specification and the appended claims, "bibulous" is understood to mean absorbent.) A series of notches in the intermediate layer surround the space around and above the assay areas to constrain the flow of sample to these areas. In another embodiment, an elongated, substantially rectangular slot in the intermediate layer guides the sample to a succession of bibulous areas that are separated by a non-bibulous region.

A fixed volume of sample—typically whole blood that includes both red cells and glucose—is thus directed to the sample side of the membrane at each of a series of assay areas. The porosity of the matrix permits fluid to pass from the sample side toward the testing side, for example by capillary action. Thus, the testing reagent can react with glucose in the blood to cause a color change on or near the testing side. Since the strongly-colored red cells can make it harder to detect the color change, the matrix is preferably anisotropic, with pore sizes graduated from large pores on the sample side to smaller pores on the testing side, in order to trap red cells away from the testing side. A variety of materials may be used for the various components of the test strip and timer of this invention. Some of these materials are disclosed in U.S. Pat. Nos. 5,306,623 and 5,418,142, issued Apr. 26, 1994 and May 23, 1995, respectively, to Kiser et al., and incorporated herein by reference.

The testing reagent comprises a component for converting glucose to hydrogen peroxide, such as glucose oxidase; one or more components for detecting the hydrogen peroxide produced from the glucose present in the sample; and an inhibitor. The components for detecting hydrogen peroxide may be a peroxidase, preferably horseradish peroxidase, together with an "indicator" that changes color in the course of the reaction. The indicator may be an oxidizable dye or a dye couple. The peroxidase catalyzes the oxidation of the indicator in the presence of hydrogen peroxide. The final element of the reagent is an inhibitor that retards the color-changing oxidation of the indicator.

The strip is segmented along its length in such a way that adjacent membrane segments have different inhibitor concentrations. Each segment has a bibulous assay area that only changes color if and when enough glucose is present to first cause all the inhibitor to be consumed and to then oxidize the indicator and thereby cause the characteristic color change. Thus, a color change in a particular area evidences a threshold glucose concentration in the original blood sample. Along the strip, in a particular direction, each successive segment has a stepwise greater inhibitor concentration, which corresponds to a stepwise increase in threshold glucose concentration. The indicator concentration is the same for all segments. In principle, other varying inhibitor/indicator balances are also possible.

If the segments have inhibitor concentrations in the appropriate range for a particular test sample, adjacent assay areas react with the analyte such that one area is colored and an adjacent one is not. That result indicates that the glucose concentration in the sample is at least equal to the threshold concentration required to change the color of the one area, but not as great as that required to change the color of the adjacent area.

For blood glucose monitoring, an optional timer segment coating comprises the elements of the indicator strip—a porous matrix having a testing reagent coated on it—and, in addition, glucose. In the dry state, the reagent chemistry is not activated by the glucose, but when a sample is applied to the strip, the timer coating is hydrated and the glucose in the coating, after a predetermined time, causes the indicator to change color. Preferably glucose is present in the timer in an amount well in excess of that required to overcome the inhibitor. In that case, the time required is longer or shorter depending on whether more or less inhibitor is present. Color changes in the strip and in the timer can be observed either directly by the eye or with an optical instrument that detects changes in reflectance.

BRIEF DESCRIPTION OF THE DRAWINGS

FIG. 6 is a top plan view, showing the testing side of the test strip of FIG. 5.

FIG. 7 is the strip of FIG. 6 after a sample has been applied to it.

FIG. 8 is a cutaway perspective view of another embodiment of the test strip of FIG. 2.

DETAILED DESCRIPTION OF THE INVENTION

Figure 1:
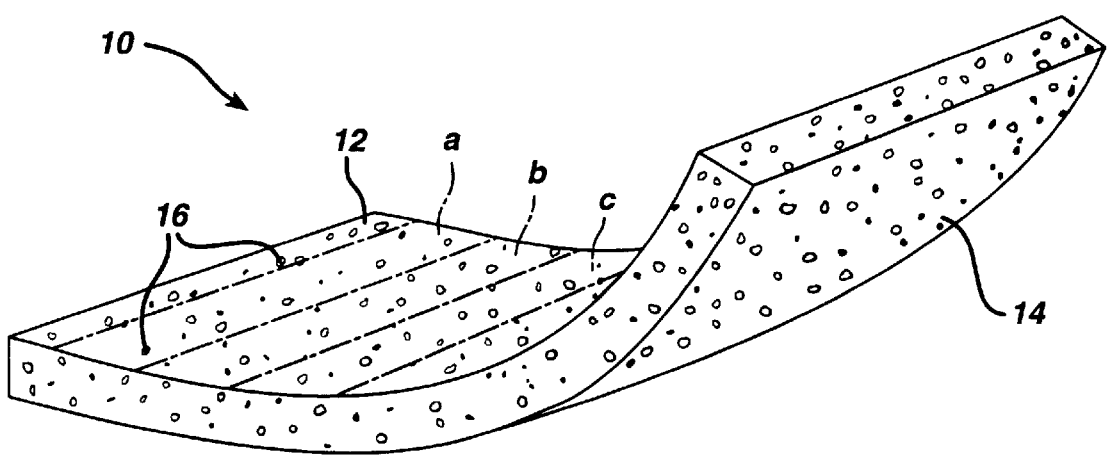
FIG. 1 is a perspective view of the matrix of a direct-reading reagent test strip of the present invention.

The present invention is a direct-reading reagent test strip for measuring concentration of an analyte in a biological fluid. The key element of such a test strip is a porous matrix that incorporates a testing reagent that undergoes a color change in response to the analyte in a biological fluid sample that is applied to the strip.

The matrix may be of a uniform composition or may be a coated substrate and may be either isotropic or anisotropic. It has a sample side, to which the sample is applied, and a testing side, where the color change is observed. Preferably, the matrix is an anisotropic membrane; more preferably, an anisotropic membrane having a broad range of pore sizes.

For example, a gradient of pore sizes from about 0.1 micrometers to about 150 micrometers may extend through the membrane. On the large-pore side, pore size is preferably in the range from about 30 micrometers to about 40 micrometers. On the side of the membrane where the pores are smallest, the void volume is relatively small, and the material of the membrane is generally quite dense, within a layer that can typically constitute up to 20% of the membrane's thickness. Within this layer, pore size is preferably in the range from about 0.1 to about 0.8 micrometers, with a nominal pore size preferably about 0.3 micrometers. When the biological fluid is applied to the sample side, the sample encounters increasingly smaller pores as it penetrates the membrane. Eventually, solids such as red blood cells reach a position in the membrane where they can penetrate no further. The balance of the sample, still containing the dissolved glucose, penetrates through to the testing side. The anisotropic nature of the membrane and/or use of a separating component (discussed below) permits relatively rapid flow rates through the membrane, even while filtration of the solids is taking place.

As the sample passes through the matrix, reaction with the reagent causes a light-absorbing dye to be formed or decomposed in the void volume near the testing side, thereby substantially affecting reflectance from the matrix.

Polysulfones and polyamides (nylons) are examples of suitable matrix materials. Other polymers having comparable properties may also be used. The polymers may be modified to introduce other functional groups which provide for charged structures, so that the surfaces of the matrix may be neutral, positive, or negative.

A preferred method of preparing the porous material that forms the matrix is to cast the polymer without a supporting core. Such a matrix is, for example, the anisotropic polysulfone membrane available from Memtec, Inc., Timonium, Md. A matrix of less than about 200 micrometers thickness is usually employed, with about 115 to 155 micrometers being preferred. A thickness of about 130 to 140 micrometers is most preferred, particularly when the matrix is nylon or anisotropic polysulfone.

The membrane may be treated with testing reagent by dipping it into an admixture of the components, thereby saturating the membrane. Preferably, at least some of the components are applied to the membrane sequentially. Excess reagent may be removed by mechanical means such as, for example, an air knife, doctor blade, or glass rod. The membrane is then dried. Reagent tends to concentrate near the small-pore (testing) side of the membrane.

The testing reagent comprises (i) a component for converting glucose to hydrogen peroxide, (ii) a component for detecting hydrogen peroxide, and (iii) a component for inhibiting the component that detects the hydrogen peroxide. The reagent may optionally further comprise a separating component which causes solids, such as red blood cells, to become entrapped in the matrix, effectively removing the solids from the biological fluid. Additional components may also be included as described hereinbelow and in the Examples.

Preferred components for converting glucose to hydrogen peroxide include glucose oxidase, an enzyme that is usually obtained from Aspergillus niger or Penicillium. Glucose oxidase reacts with glucose and oxygen to produce gluconolactone and hydrogen peroxide. Optimum glucose oxidase concentration depends on the composition of the indicator system. For example, if the indicator system is MBTHSB-ANS (which is described below), then glucose oxidase in the range from about 500–10,000 U./mL is suitable, more preferably from about 700–2000 U./mL, and most preferably about 1000 U./mL. Generally, higher concentrations of glucose oxidase cause the reaction to proceed more rapidly and lower concentrations, less rapidly.

The hydrogen peroxide so produced reacts with the component for detecting hydrogen peroxide, which comprises a peroxidase that selectively catalyzes a reaction between the hydrogen peroxide and an indicator. The peroxidase uses hydrogen peroxide as an oxidant which is capable of removing hydrogen atoms from various substrates. A suitable peroxidase may contain ferriprotoporphyrin, a red hemin obtained from plants. Peroxidases obtained from animals, for example from the thyroid glands of animals, are also suitable. Horseradish peroxidase (HRPO) is especially preferred as a constituent of the component for detecting hydrogen peroxide.

The hydrogen peroxide, preferably catalyzed by a peroxidase, reacts either directly or indirectly to form or decompose an indicator dye that absorbs light in a predetermined wavelength range. Preferably, the indicator dye absorbs strongly at a wavelength different from that at which the testing reagent absorbs strongly. The oxidized form of the indicator may be the colored, faintly-colored, or colorless final product that evidences a change in color of the testing side of the matrix. That is to say, the testing reagent can indicate the presence of analyte in a sample by a colored area being bleached or, alternatively, by a colorless area developing color.

Indicators that are useful in the present invention include (a) 3-methyl-2-benzothiazolinone hydrazone hydrochloride (MBTH) combined with 3-dimethylaminobenzoic acid (DMAB); (b) MBTH combined with 3,5-dichloro-2-hydroxybenzene-sulfonic acid (DCHBS); (c) 4-aminoantipyrene (4-AAP) and 5-oxo-1-(p-sulfophenyl)-2-pyrazoline-3-carboxylic acid (OPSP); (d) 4-AAP and N-(m-tolyl)-diethanolamine (NDA); (e) 2,2'-azino-di (3-ethylbenzthiazoline) sulfonic acid (ABTS); (f) 4AAP and 4-methoxynaphthol; (g) pyrogallol red (PGR); (h) bromopyrogallol red (BPR); (i) Acid Green 25 (AG); or (j) [3-methyl-2-benzothiazolinone hydrazone]N-sulfonyl benzene-sulfonate monosodium (MBTHSB), combined with 8-anilino-1-naphthalene sulfonic acid ammonium (ANS). MBTHSB-ANS is preferred. Additional information regarding MBTHSB-ANS appears in U.S. Pat. No. 5,563,031, issued Oct. 8, 1996, and incorporated herein by reference.

The inhibiting component retards the reaction between the hydrogen peroxide and the indicator, for example by reducing the hydrogen peroxide or by reducing the oxidized indicator. In principle there are several different modes of operation for an inhibitor. First, the inhibitor could compete with the indicator and thereby slow the rate at which the color change takes place in the indicator. Second, the inhibitor could be non-competitive, so that substantially all the inhibitor is consumed before any substantial color change takes place in the indicator. Other modes of inhibitor operation are also possible. Preferably, inhibitors of the present invention are non-competitive.

Among the range of suitable inhibitors are 2,3,4-trihydroxybenzoic acid; propyl gallate; 3,4 dihydroxy cinnamic acid; 3,4 dihydroxy benzaldehyde; gallic acid; 5,6-diaminouracil; ascorbic acid; and isoascorbic acid. Ascorbic acid is preferred; however, ascorbic acid oxidizes in solution and must be stabilized in order to permit the reagent to be coated. Preferred stabilizers are primary alcohols, such as ethyl, methyl, or propyl alcohol. Ethyl alcohol is preferred, particularly concentrated solutions; i.e., solutions of 50% or more ethanol.

Although the anisotropic membrane that is the preferred matrix filters out red blood cells and holds them away from the testing side, optionally the testing reagent may also contain a separating component. The separating component should be capable of producing a relatively clear colorless fluid from fluid containing red blood cells, e.g., whole blood, by sequestering red blood cells in the matrix. Separating components for use in the instant invention include but are not limited to polyethylene glycol, poly (methylvinyl ether/maleic) anhydride, polypropylene glycol, polystyrene sulfonic acid, polyacrylic acid, polyvinyl alcohol, and polyvinyl sulfonic acid at a pH of between about 4.0–8.0. Such separating components are present in the matrix in amounts that will vary depending upon their charge and molecular weight, the other components imbedded in the matrix, the matrix pH and pore size, and the residual moisture of the matrix after drying. Such parameters are readily determinable by one skilled in the art. For example, when polypropylene glycol is employed as the separating component (e.g., PPG-410 from BASF, Wyandotte, Mich.), it is preferably present at about 2–30% weight to volume (w/v), and more preferably 8–10% w/v. Other separating components can also be employed in a concentration of about 2–30% w/v. The polymeric separating components may be impregnated or imbedded in the matrix or cast in the membrane during manufacture.

Some water soluble salts can also effect blood separation. Among salts suitable for separating blood components are citrates, formates, and sulfates, as well as certain acids, such as amino acids, citric acid, phytic acid, and malic acid. (See, e.g., U.S. Pat. No. 3,552,928, issued Jan. 5,1971, to M. C. Fetter.) An advantage of including the separating component is that with solids such as red blood cells substantially removed from the biological fluid, there is less background color at the test site to obscure a change in coloration produced by the testing reagent.

Other components may be imbedded into the matrix to enhance the coloration and readability of the reagent strips and to preserve the uniformity and integrity of the matrix. For example, the testing reagent may include salts and/or buffers to aid in the separation of the dye in the matrix. Such buffers may contain for example, citrate, present in solution at from about 0.01M to about 1.0M, and preferably at about 0.1M. Other buffers may also be employed.

Compounds that make the matrix hydrophilic or compounds that can act as stabilizers, such as hydrolyzed proteins, may also be employed. Such compounds include but are not limited to for example bovine serum albumin, polypeptides and the low molecular weight protein available as Crotein SPA (CRODA, Inc. New York, N.Y.). Such compounds are used at concentrations of for example about 1 mg/mL to about 100 mg/mL. In the case of Crotein, about 30 mg/mL is preferred.

Other stabilizers and preservatives may also be included in the coating for the matrix. For example ethylene diamine tetraacetic acid (EDTA), diethylene triamine pentaacetic acid (DTPA) and related compounds may be employed, for example, at concentrations of about 0.01 mg/mL to about 10 mg/mL. Among the purposes of the preservatives is to help to stabilize the inhibitor.

Some of the indicators (e.g., BPR) have an undesirable tendency to migrate in the matrix. When such an indicator is used, an ion pairing agent is included to prevent such migration. For example, the polyethylene glycol derivatives commercially available as Polyquart (H) (Henkel, Inc., Ambler, Pa.) are particularly useful for their ability to facilitate ion pairing between the indicator and other matrix substituents.

When the presence of an analyte is indicated by color formation (e.g., MBTHSB-ANS), surfactants may be added to brighten the color and enhance the contrast with the uncolored surround.

Organic solvents may also be employed in the practice of this invention and may be included in the formulation of the testing reagent for the matrix, provided, of course, that they are compatible with the matrix and testing reagent compositions. Potentially suitable organic solvents include chloroform, acetone, alcohols, methylene chloride, diethyl and petroleum ethers, acetonitriles, and mixtures thereof. In the practice of the present invention, 70% ethanol in water is particularly preferred.

The testing reagent that is coated on or impregnated into the matrix is not uniform over the surface of the test strip. Instead, the reagent is preferably applied to the matrix in a series of parallel stripes, or "segments," that extend across the narrow dimension of the strip. The composition in adjoining segments increases, stepwise, in inhibitor concentration. Each segment has a bibulous assay area. It is in the assay areas that the testing reagent reacts with any glucose in the blood to cause a color change, provided that the glucose concentration is large enough to overcome the inhibitor level in that assay area. Thus, each succeeding assay area requires, stepwise, a greater glucose concentration in the sample to cause the area to change color.

Optionally, one of the assay areas is adapted to serve as a timer, to indicate that enough time has elapsed for the reagent to react with the glucose on each of the assay areas. The timer segment of the matrix is coated or impregnated with a composition that consists of the testing reagent and, in addition, glucose. Since the testing reagent's purpose is to change color in response to glucose, combining the two without causing the color change requires some care. An amount of inhibitor beyond that required for the timing function must be present to compensate for this effect. The rate at which the timer segment is dried, after the glucose containing solution is applied, is controlled. In practice, the membrane is first coated with a solution containing buffers, stabilizers, and enzymes, and that coating is dried to form a first layer. Then, a second coating pass applies a solution containing indicator, inhibitor, and glucose. Parameters such as web speed, oven temperature and airflow, and quantity of coating solutions deposited will have been fixed beforehand and appropriate adjustments made to the inhibitor and/or glucose concentrations. Instead of applying the second coating directly, an alternative, less preferred, involves making the second coating on a separate web and then placing it over the first layer.

When a sample is applied to the strip, hydration of the timer segment composition permits the color-forming reaction to proceed. The time it takes for the timer segment to change color is then determined by the temperature and by characteristics of the testing reagent, particularly the inhibitor concentration, the amount of glucose, and the hydration and oxygen diffusion rates.

The timer color-change time can be made to depend on the glucose concentration in the sample or, alternatively, to be independent of that concentration. By incorporating a great excess of glucose in the timer, the time is substantially independent of the sample's glucose concentration. By incorporating less glucose in the timer, the time may be made to depend on the glucose in the sample; i.e., the timer will change color faster if glucose concentration in the sample is greater. Preferably, the glucose concentration in the timer is greater than about 1500 mg/dL, which makes the timer substantially independent of the sample glucose concentration in the range from about 40–400 mg/dL. The timer segment composition includes excess amounts of the component (such as glucose oxidase) that converts glucose to hydrogen peroxide and of glucose. The timer composition should then include at least as much, or more, inhibitor than does the result segment that has the highest inhibitor concentration (which corresponds to the highest glucose reading).

The timer also serves an important quality-control function, by making it apparent when a test strip has been compromised by exposure to moisture. The test strip must remain dry until the time it is to be used, because components that convert glucose to hydrogen peroxide (generally enzymes) tend to degrade on exposure to moisture. Thus, if the strip is prematurely exposed to moisture, it will become compromised. But the impairment of the test strip is not apparent to a user, who may, therefore, use such a strip and get an erroneous result. However, if the strip includes a timer segment, exposure to moisture causes the timer to change color, which alerts the user to the fact that the strip has been compromised and should not be used.

Additional information concerning the timer appears in copending U.S. patent application Ser. No. 08/706,753, filed Sep. 3, 1996, and incorporated herein by reference.

In addition to the reagent-containing matrix, the strip of the present invention includes a bottom layer that supports the matrix. The bottom layer is preferably a thermoplastic sheet, more preferably a polyester, generally about 0.05–0.2 mm thick, and has a hole through which sample may be applied to the sample side of the matrix. From the sample hole the blood sample is distributed along the length of the matrix. If the bottom layer is generally opaque, then one or more transparent window sections may be located an appropriate distance from the sample hole, the appearance of sample in the window(s) confirming that adequate sample has been applied to the strip.

Distributing the blood from the sample hole to the assay areas involves an intermediate layer that lies between the bottom layer and the membrane and, optionally, is adhered to both of them. The intermediate layer is preferably a thermoplastic sheet; more preferably a polyester, generally about 0.05–0.2 mm thick. In one embodiment, cutouts in the intermediate layer guide the sample down the length of the strip along non-bibulous paths on the membrane and direct the sample to each of the assay areas. Notches in the intermediate layer align with the assay areas, so that each assay area is substantially surrounded by the walls of the intermediate layer. In another embodiment, the intermediate layer has an elongated, substantially rectangular slot that guides the sample across the membrane surface to the assay areas. Slot width is generally in the range between about 0.5 and 3 mm.

A preferred structure for the non-bibulous paths on the membrane is formed by collapsing the membrane pore structure. That can be accomplished by heating, either directly or by using a laser or ultrasound, and preferably including pressure. However, the preferred method is crushing. Thus, the membrane is crushed to make it non-bibulous (but still hydrophilic) everywhere, except for the assay areas. In one embodiment of the invention, the membrane is crushed between flat plates, with a die preventing the assay areas from being crushed. Pressures of at least about 6 tons/in$^2$ (80,000 kPa) are preferred. Optionally, the plates may be heated to at least about 110° C. The preferred pressures and temperatures depend, of course, on the crush mechanism and dwell time, as well as the membrane parameters. Optimum values can be determined by routine experimentation. The embodiment in which the membrane is crushed in this manner yields assay areas that extend toward the bottom layer and is used with the notched intermediate layer, as discussed below.

For precise measurements, the volume of blood provided to each assay area is preferably reproducible. If the notches entirely encircled the assay areas, then, assuming a liquid-tight seal between the intermediate layer and both the bottom layer and the crushed membrane, each assay area would be associated with a closed (cylindrical) volume whose walls are formed by the intermediate layer and whose ends are formed by the membrane and bottom layers. However, a distribution channel runs along the strip and feeds sample to each of the assay areas. Preferably, the bottom layer has vent holes in alignment with the assay areas to facilitate filling the channel and assay areas uniformly. High precision requires that the distribution channel provide a fixed volume of sample to each assay area but then provide no more, at least not in the time frame of the measurement—about 1 or 2 minutes, starting about 90 seconds after blood is applied. Since the initial sample volume is variable, there is preferably an absorbent layer at each end of the membrane to carry off excess sample from the ends of the distribution channel. Absorbent layers at the ends of the channel also enhance wicking of the sample along the length of the strip. Nonwoven fabrics, well known in the art, form the preferred absorbent layers.

In another embodiment of the invention, the membrane and cover sheet are pressed between rollers. The cover sheet has holes positioned to accommodate the assay areas, and these areas then extend into those holes, remaining uncrushed. For this embodiment, no die is needed, and crushing is preferably accomplished by rollers, with an applied force of at least about 1000 lb. (4,450N). Note that the assay areas in this embodiment extend in the opposite direction from those in the embodiment described above. Since sample is drawn toward the upper layer, open to the outside, no vent holes are used in the bottom layer. This embodiment is used with the intermediate layer that has a substantially rectangular slot to guide the sample to the assay areas. Since that embodiment has a sample hole located near the end of the strip that has the "high-glucose" assay areas, only a single absorbent layer, near the opposite end of the strip, is used.

The color change caused by glucose in the test sample appears on the testing side of the membrane. In the embodiment in which the assay areas extend toward the bottom layer, it is convenient to overlay the testing side of the membrane with an upper layer that has holes which align with the assay areas. The holes make the color changes visible and also permit oxygen to reach the reaction sites. When the assay areas extend in the opposite direction, the holes in the upper layer define the assay areas during the crushing process, as was described above. In both cases, the upper layer is preferably a thermoplastic sheet, more preferably a polyester, generally about 0.05–0.2 mm thick. The upper layer may be attached to the membrane, for example, with an adhesive. Any adhesive is preferably limited to non-bibulous areas of the membrane, if it would interfere with the glucose-measuring reactions. However, if the adhesive doesn't interfere with the reactions, its placement is less critical.

Since the assay areas, when they contain the preferred reagent, slowly undergo a color change when exposed to light or oxygen and since the optional timer is sensitive to moisture, strips are preferably packaged in an opaque oxygen- and moisture-impermeable enclosure, such as a sealed foil wrap. If strips are individually packaged, the strip may remain in the peeled-open wrap during use.

The invention will now be described further with reference to the Figures. FIG. 1 shows a matrix 10 of the present invention, for measuring the amount of analyte in a biological fluid. Although shown in an arched position, matrix 10 is flexible and is generally in a flat plane when used. The matrix includes a sample side 12, to which the biological fluid sample is applied, and a testing side 14, on or near which a change in color indicates the presence of the analyte. The color change results from the interaction of the analyte with reagent impregnated in pores 16. Preferably, for measuring the concentration of glucose in blood, pore sizes are relatively large near sample side 12 and decrease in size as testing side 14 is approached. The pore size gradient serves to trap red blood cells near sample side 12, so that their color does not interfere with the ability to see the color change that indicates the presence of the analyte.

Three parallel segments, a, b, and c, are shown schematically. Each succeeding segment has stepwise more inhibitor than the one before. In a preferred embodiment, after reagent has been applied to the membrane in parallel segments, as shown, the membrane is crushed everywhere but in the assay areas, where the analyte-reagent reactions take place. One embodiment of a pattern of bibulous assay areas—a single area located in each of the parallel segments—and non-bibulous crushed areas is depicted in the plan view of FIG. 2 and the enlarged fragmentary perspective view of FIG. 3.

Figure 2:
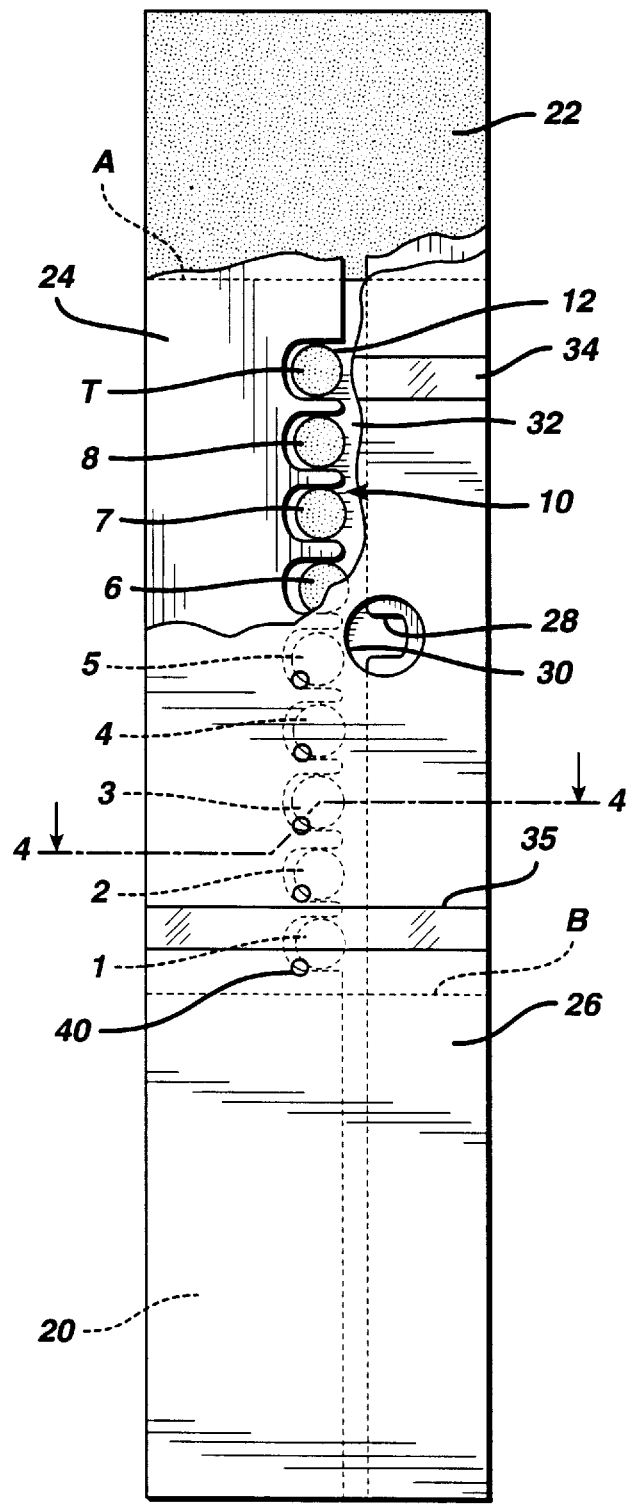
FIG. 2 is a cutaway bottom plan view of the sample side of a directreading reagent test strip of the present invention.

FIG. 2 is a bottom plan view, in partial cutaway, of the sample side 12 of membrane 10 and absorbent layers 20 and 22, overlaid with intermediate layer 24 and bottom layer 26. Membrane 10 and absorbent layers 20 and 22 are preferably supported by a top layer, not shown. Absorbent layers 20 and 22 are preferably located at the ends of the membrane (beyond dashed lines A and B) to absorb blood sample that is in excess of the volume needed for the measurement. That volume must be sufficient to provide sample to each of the assay areas and, if present, the timer area as well. In general, a strip that has fewer assay areas doesn't require as much sample, but provides a smaller range of glucose values and/or less precision. FIG. 2 shows 9 bibulous areas, representing 8 assay areas (numbered 1–8) and a timer (T), which provides adequate range and precision while not requiring unacceptably large sample volume. Intermediate layer 24 has a notch 28, which aligns with sample hole 30 in bottom layer 26. Sample is introduced through sample hole 30 and is directed by capillary action along central channel 32 of intermediate layer 24 to each of the assay areas and the timing area, any excess sample being absorbed in absorbent layers 20 and 22. The appearance of sample through optional clear windows 34 and 35 confirms that sufficient sample has been provided for measurement. Preferably, intermediate layer 24 forms a seal with sample side 12 of the membrane, so that sample cannot, for example, flow directly between adjoining assay areas.

Figure 3:
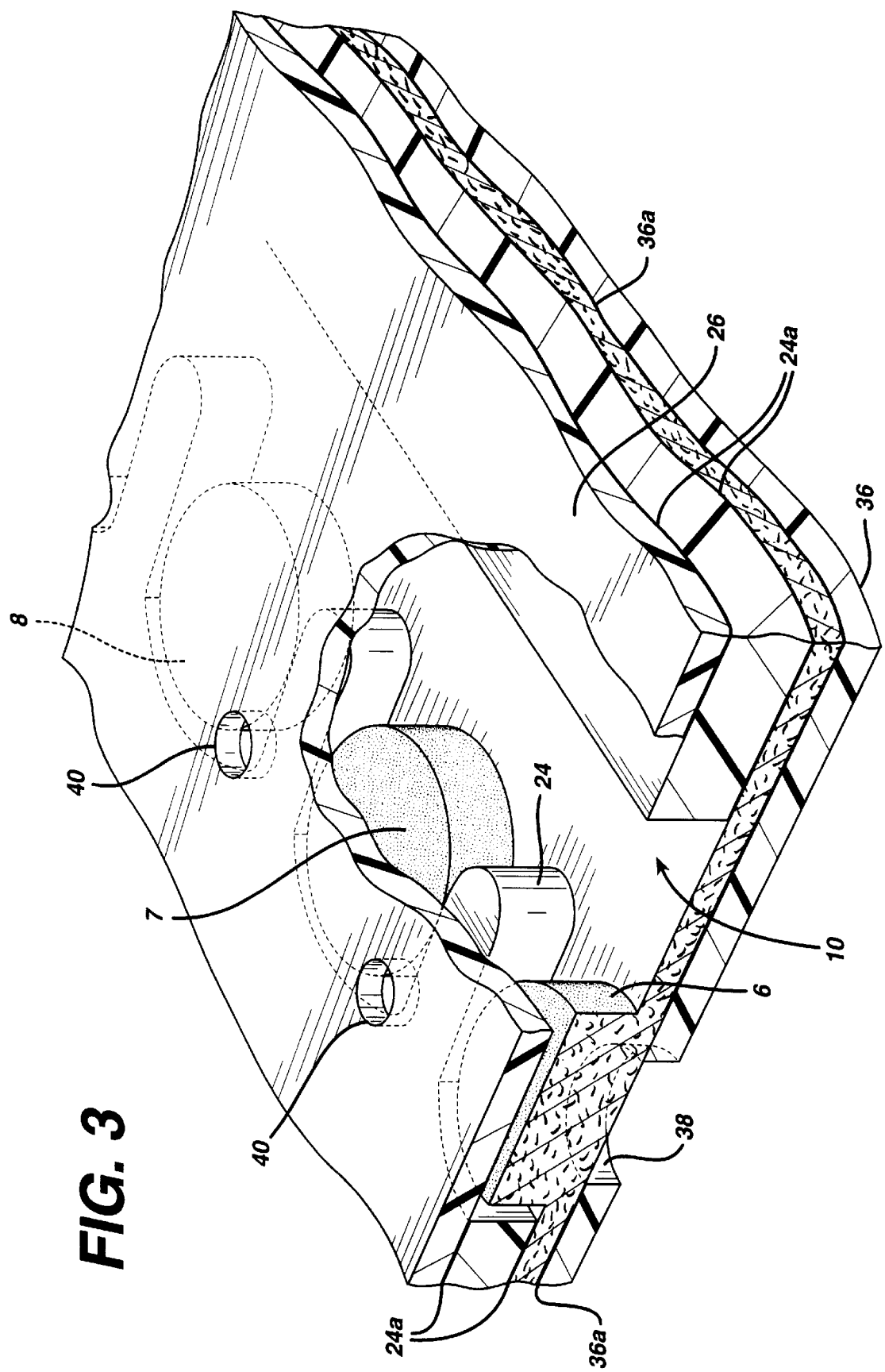
FIG. 3 is an enlarged fragmentary perspective view of the interior of the test strip of FIG. 2, partially cutaway.

FIG. 3 is an enlarged fragmentary perspective view, depicting parts of 3 assay areas, 6, 7, and 8, seen through bottom layer 26, and separated by fingers of intermediate layer 24. Optional adhesive layers 24a join intermediate layer 24 to bottom layer 26 and membrane 10. Vent holes 40 in layer 26 facilitate sample flow into the strip. Holes, such as 38, in top layer 36 line up with the bibulous areas, making visible any color change in the bibulous area and also admitting oxygen needed for the color-changing reaction. Optional adhesive layer 36a joins top layer 36 to the testing side of membrane 10.

Figure 4:
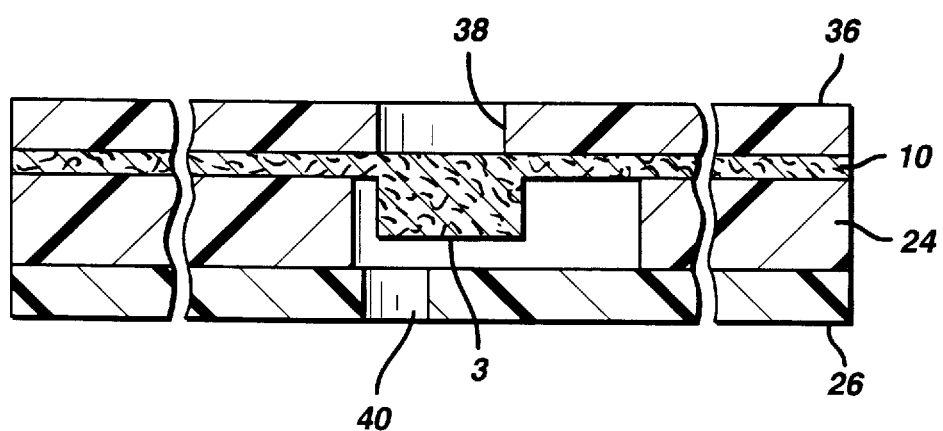
FIG. 4 is a cross section of the strip of FIG. 2 taken along line 4—4.

FIG. 4 is a cross section taken along line 4—4 of FIG. 2, which shows top layer 36, in addition to the layers shown in FIG. 2. Vent holes in bottom layer 26, such as 40, line up with the assay and timer areas and facilitate sample filling the volume surrounding each of those areas. The volumes to be filled are bounded by membrane 10, intermediate layer 24 and bottom layer 26. Note that columnar assay area 3 extends toward bottom layer 26, and the minimum separation between the assay area and bottom layer is typically only about 12 micrometers. The separation is shown larger than to scale for clarity.

Figure 5:
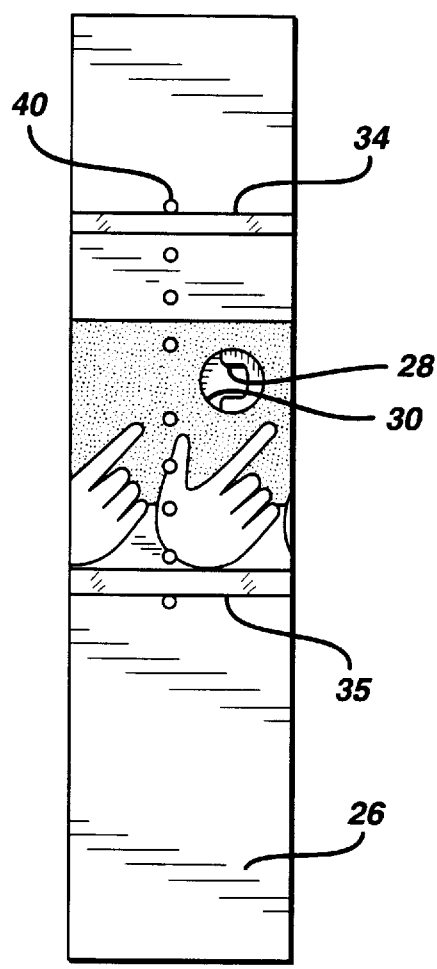
FIG. 5 is a bottom plan view of the test strip of FIG. 2.

FIG. 5 is a bottom plan view of a strip of the present invention, showing sample hole 30 and the graphics that direct the user to introduce the sample through that hole. When sample is seen through clear windows 34 and 35, it confirms that adequate sample has been applied to the strip.

FIG. 6 is a plan view of top layer 36 of a strip that has been calibrated to associate assay areas with glucose concentration.

FIG. 7 shows the strip of FIG. 6 after a blood sample has been applied to opening 30 (FIG. 2), the sample has spread along central channel 32, and glucose in the sample has reacted with the reagent in the assay areas. Since the bottom assay area has the least inhibitor, that area will have changed color first. Thereafter, the second and then the third area changed color. The upper circles did not change color, because there was too little glucose in the sample. Since enough time has elapsed for timer area 42 to change color, the strip can be read. Thus, the result depicted in FIG. 7 indicates that the sample glucose concentration is at least 120 mg/dL, but less than 150 mg/dL. The reading can be taken at any time after timer area 42 changes color. Note that in FIG. 7 the color change caused by the reaction with glucose is from white to colored. However, the system could alternatively operate with an indicator dye that is destroyed by the glucose-induced oxidation, with a corresponding color change from colored to white.

FIG. 8 is a cutaway perspective view of another embodiment of the strip of this invention. Bottom layer 126 has sample hole 130 for introducing the blood sample. Unlike the embodiment of FIG. 2, where sample hole 30 is located near the middle (end-to-end) of the strip, sample hole 130 is preferably located near the end of the strip that has assay areas to indicate a high glucose concentration, as well as the optional timer. Positioning the sample hole at that end provides two advantages. First, the time needed for the glucose measurement is reduced by the reduced time for blood to reach the "high-glucose" assay areas (which take the longest to respond). Second, timer variability is reduced, because the sample is essentially applied directly to the timer, eliminating variability in time for blood to reach the timer. Intermediate layer 124 has an elongated slot 132 that runs the length of the strip from a cutout that generally corresponds to, and is in alignment with, sample hole 130. The slot channels the blood sample along the length of the strip, over membrane 110, toward absorbent layer 120. As the sample passes over membrane 110, part of it is deposited in the timer T' and in each of the eight assay areas (numbered 101–108). The timer and assay areas are each viewed through corresponding holes in top layer 136 that are aligned with them. Appearance of blood through clear window 135 confirms that sufficient sample has been provided for measurement.

Figure 9:
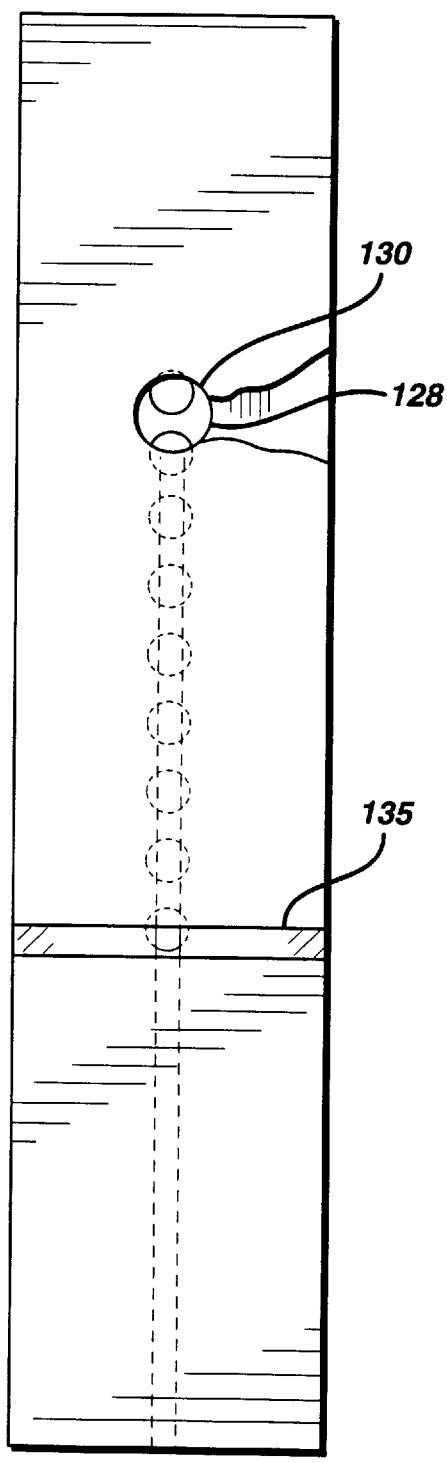
FIG. 9 is a bottom plan view of the test strip of FIG. 8.

FIG. 9 is a bottom plan view of the strip of FIG. 8, in which the graphics (such as depicted in FIG. 5) that direct the user to introduce the sample through hole 130 in the bottom layer (and co-aligned hole 128 in the intermediate layer) have been omitted.

Figure 10:
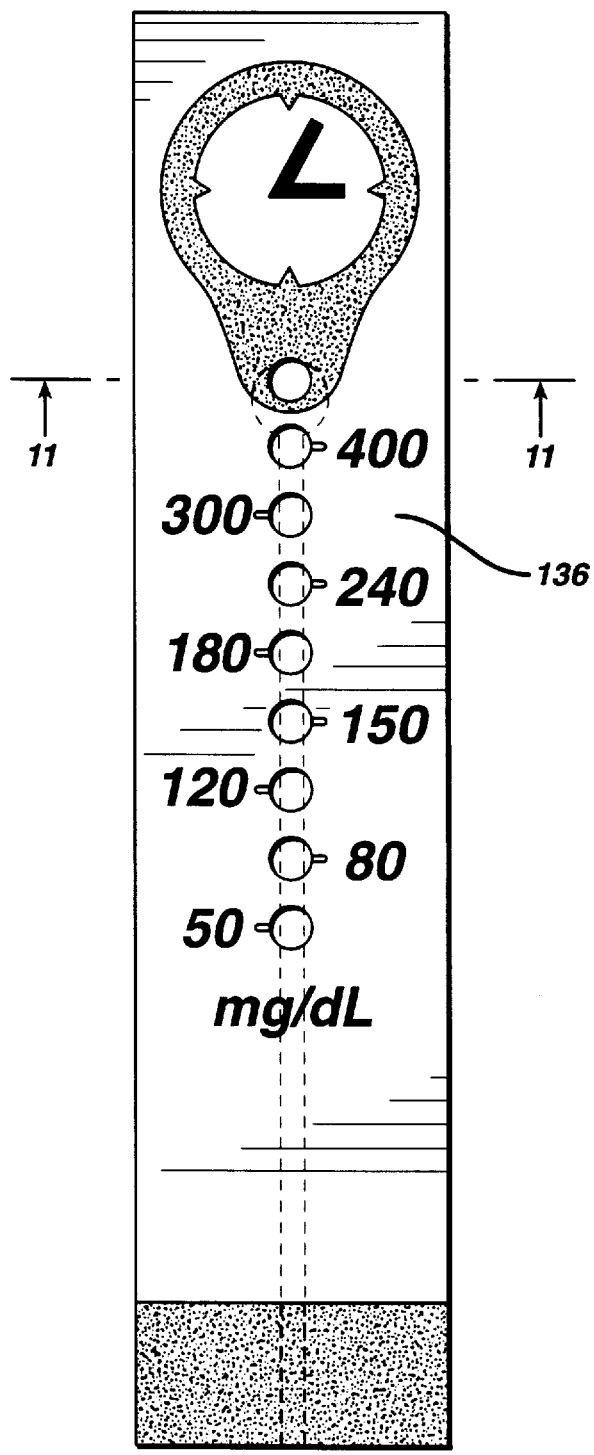
FIG. 10 is a top plan view of the test strip of FIG. 8.

FIG. 10 is a plan view of top layer 136 that shows the timer graphics, as well as the calibration of the assay areas.

Figure 11:
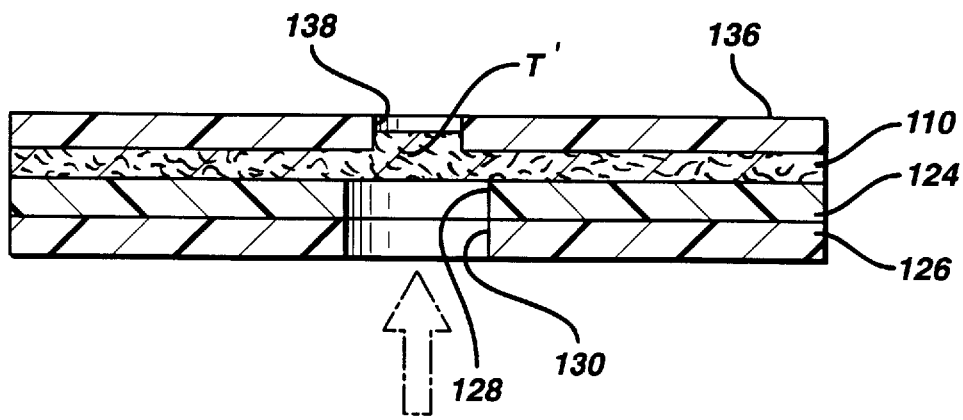
FIG. 11 is a cross section of the strip of FIG. 10 taken along line 11—11.

FIG. 11 is a cross section taken along line 11—11 of FIG. 10, which shows top layer 136, membrane 110, intermediate layer 124 and bottom layer 126. The arrow illustrates the direction of sample introduction into hole 130, in bottom layer 126, and co-aligned hole 128, in intermediate layer 124. Note that columnar timer area T' extends upward toward, and preferably into, corresponding hole 138, which is aligned with timer T' and is one of the nine holes in top layer 136 that are aligned with the corresponding timer and assay areas.

For a better understanding of the present invention, the following Examples further illustrate various embodiments of the invention. The Examples are not intended to be in any way limiting.

EXAMPLE 1

BPR INDICATOR

The following solution was prepared:            Enzyme Solution

| Distilled Water | 83.5 g | 0.2M Aconitic Acid | 27.0 g |
|---|---|---|---|
| 1% (w/w) EDTA Na$_2$ | 23.8 g | Glucose Oxidase | 165,000 U |
| Aconitic Acid | 6.0 g | HRPO | 340,000 U |
| NaOH (solid) | 2.2 g | | |
| Crotein SPA | 4.2 g | | |
| Imidazole | 0.6 g | | |
| Mannitol | 3.0 g | | |
| 5% (w/w) Surfactol Q1 | 3.0 g | | |
| Adjust pH to 4.80 | | | |
| Ethyl Alcohol | 40.0 g | | |
| PPG-410 | 5.6 g | | |
| Enzyme Solution | 28.0 g | | |

Memtec BTSH 55 membrane was immersion coated in this solution and the excess doctored off with glass rods. The coated membrane was dried in a flotation dryer at 180° F. under moderate airflows so that the web was substantially dry within 20 seconds. The web was spooled in preparation for the second coating, described below.

The following solutions were prepared:

| Ascorbate (inhibitor) stock solution | | Diluent |
|---|---|---|
| Distilled Water | 190 g | 370 g |
| 1% EDTA Na$_2$ | 55 g | 107 g |
| BPR | 0.36 g | 0.71 g |
| PolyQuart ® H | 6 g | 11.8 g |
| PPG-410 | 14.2 g | 27.8 g |
| Ascorbic Acid | 1.37 g | — |
| Ethyl Alcohol | 243 g | 477 g |

Timer Solution

| Diluent (per above formula) | 120 g |
|---|---|
| Ascorbic Acid | 0.885 g |
| Glucose Solution* | 17.25 g |

*The Glucose Solution is a 16.0 g/dL solution of glucose in water allowed to mutarotate for 24 hours, stored refrigerated.

The following dilutions of the stock solution were made: 0.0405:1, 0.108:1, 0.236:1, 0.369:1, 0.569:1, 1.260:1. This stepwise increase in inhibitor concentration corresponds to the stepwise-greater glucose concentration that the assay areas report. These solutions, along with the timer solution, were coated side-by-side onto the large-pore side of the enzyme-loaded membrane so as to deposit approximately $1.2 \times 10^{-4}$ mL per square millimeter of membrane. The membrane was wet approximately fifteen seconds before experiencing the same drying conditions as described above for the enzyme coating step. Results showed the timer reacting in about 70 seconds with about 95% of results falling between 64 and 79 seconds.

EXAMPLE 2
MBTHSB-ANS INDICATOR

The following solution was prepared:

| | |
|---|---|
| HPLC water | 1500 mL |
| Citric Acid | 16.92 g |
| Sodium Citrate | 20.88 g |
| Mannitol | 15 g |
| Disodium EDTA | 1.26 g |
| Gantrez S95 | 6.75 g |
| Crotein SPA | 36 g |
| Glucose Oxidase | 1.69 MU |
| HRPO | 1.5 MU |
| Carbopol 910* | 75 mL |
| Disodium Citrate** | 225 mL |

*11% solution in Acetonitrile
**0.1M, pH 5.0

Memtec BTS 35 membrane was coated in a trough so that the large-pored surface contacted the coating solution; excess solution was removed with glass rods as before. The membrane was dried and spooled as in Example 1.

The following solutions were made:

| Solution A (Indicator) | |
|---|---|
| 70% (v/v) Ethanol | 2819 mL |
| MBTHSB | 2.98 g |
| (NH$_4$) ANS | 25.83 g |
| Solution B | 205 mL |
| 2% DTPA | 51.25 mL |
| Solution B (Wetting Agent) | |
| Maphos ® 60A | 41 g |
| 70% (v/v) Ethanol | 205 mL |
| Solution C (Ascorbate Stock) | |
| Water | 115 mL |
| Ascorbic Acid | 4.58 g |
| Ethanol | 267 mL |
| Solution D (Timer) | |
| Water | 53 mL |
| Ascorbic Acid | 8.75 g |
| Ethanol | 123 mL |
| Bring volume to 175 mL with 70% EtOH | |
| Glucose Solution | 40.5 mL |

For each inhibitor solution, the volume of Solution A was fixed at 263 mL. For the various assay areas, the ratio of 70% EtOH:Solution C was varied from 58.9 to 0.200 so that the volume of 70% EtOH+Solution C added to Solution A was 87.5 mL for all inhibitor solutions. This effectively altered only the concentration of inhibitor in each solution. The solutions containing the stepwise-increasing inhibitor concentration and the timer solution (Solution D) were coated side-by-side onto the large-pore side of the membrane. Deposition rate was adjusted to achieve $\sim 8 \times 10^{-5}$ mL of inhibitor per square millimeter of membrane. The membrane was dried as above, except that the delay between coating and drying was about 1.6 minutes. Results showed the timer reacting in about 60 seconds with little effect from blood hematocrit from 30 to 55% or glucose from 78 to 420 mg/dL.

It will be understood by those skilled in the art that the foregoing description and Examples are illustrative of practicing the present invention but are in no way limiting. Variations of the detail presented herein may be made without departing from the scope and spirit of the present invention.

We claim:

1. An elongated multilayer reagent test strip for measuring the concentration of analyte in a sample of biological fluid that is applied to the strip, comprising
   a) a bottom layer with a through hole for accepting the sample;
   b) a membrane layer, having a sample side facing the bottom layer and a testing side opposite to it, and having arrayed along its length a plurality of discrete bibulous assay areas, separated by a non-bibulous region, the membrane containing a reagent that can react with the analyte to produce a color change, the reagent comprising:
      i) a first component that interacts with the analyte to form hydrogen peroxide;
      ii) a second component that interacts with the hydrogen peroxide to undergo a color change; and
      iii) a third component that inhibits the change in color of the second component;
   c) an intermediate layer between the bottom and membrane layers; and
   d) metering means for distributing sample along the strip, the metering means comprising a fluid transport channel formed in the intermediate layer for guiding sample over the membrane surface to the bibulous assay areas the inhibitor concentration increasing in a predetermined way with distance from a first end of the strip, so that a correspondingly increasing analyte concentration must be contained in a sample if it is to effect a color change, whereby one or more assay areas may change color when a sample is applied to the strip, and the color-changing area most distant from the first end indicates the analyte concentration in the sample.

2. The strip of claim 1 in which the analyte is glucose.

3. The strip of claim 1 in which the biological fluid is blood.

4. The strip of claim 1 in which the bottom layer comprises a thermoplastic sheet.

5. The strip of claim 4 in which the bottom layer comprises polyester.

6. The strip of claim 1 in which the bottom layer further comprises a plurality of through holes in alignment with the assay areas.

7. The strip of claim 1 in which the bottom layer has a transparent section located a predetermined distance from the sample-accepting hole to ensure adequate sample size.

8. The strip of claim 1 in which the membrane layer comprises an anisotropic porous membrane having pores that are larger near the sample side and smaller near the testing side.

9. The strip of claim 8 in which the biological fluid is whole blood that contains red blood cells.

10. The strip of claim 9 in which the pore sizes are selected so that the red blood cells of the whole blood sample are trapped in the membrane.

11. The strip of claim 8 in which the membrane comprises polysulfone.

12. The strip of claim 1 in which the fluid transfer channel is substantially rectangular.

13. The strip of claim 1 in which the first component comprises glucose oxidase.

14. The strip of claim 1 in which the second component comprises a peroxidase and an indicator dye or dye couple that changes color when it is oxidized.

15. The strip of claim 14 in which the peroxidase is horseradish peroxidase.

16. The strip of claim 14 in which the indicator dye or dye couple is [3-methyl-2-benzothiazolinone hydrazone]N-sulfonyl benzenesulfonate monosodium combined with 8-anilino-1-naphthalene sulfonic acid ammonium (MBTHSB-ANS).

17. The strip of claim 1 in which the third component comprises ascorbic acid.

18. The strip of claim 1 in which the reagent further comprises a separating component selected from the group consisting of polyethylene glycol, poly (methylvinyl ether/maleic) anhydride, polypropylene glycol, polystyrene sulfonic acid, polyacrylic acid, polyvinyl alcohol, and polyvinyl sulfonic acid.

19. The strip of claim 1 in which the intermediate layer comprises a thermoplastic sheet.

20. The strip of claim 1 in which the intermediate layer comprises polyester.

21. The strip of claim 1 in which the bibulous areas and non-bibulous region comprise uncrushed and crushed regions of the membrane layer, respectively.

22. The strip of claim 21 in which the uncrushed bibulous areas are substantially columnar, each with a base in the membrane and, opposite the base, an end that adjoins the bottom layer.

23. The strip of claim 21 in which the uncrushed bibulous areas are substantially columnar, each with a base in the membrane and, opposite the base, an end that adjoins the top layer.

24. The strip of claim 1 further comprising a top layer that is contiguous with the top surface of the membrane layer and has through holes that align with the assay areas.

25. The strip of claim 24 in which the membrane layer is adhered to the top layer.

26. The strip of claim 25 in which the membrane layer is adhered to the top layer with an adhesive that is restricted to the non-bibulous region of the membrane layer.

27. The strip of claim 1, further comprising an absorbent layer that contacts the end of the membrane that is nearest the first end of the strip.

28. The strip of claim 1 further comprising absorbent layers that contact each end of the membrane layer.

29. The strip of claim 30, in which the through hole for accepting the sample is near the end of the strip that is distal from the first end.

30. The strip of claim 1 further comprising a timer element, which comprises an assay area that includes, in addition to the reagent, an amount of glucose that causes the area to change color a predetermined time after the sample is applied to the strip.

31. A method for measuring a concentration of analyte in a sample of biological fluid, comprising the steps of:
  (a) applying the sample to a reagent test strip that comprises:
    (i) a bottom layer with a through hole for accepting the sample,
    (ii) a membrane layer, having a sample side facing the bottom layer and comprising a plurality of bibulous assay areas that each change color when contacted with fluid containing at least a predetermined amount of analyte, greater than the amount of analyte that causes a change in color of the assay areas that are closer to a first end of the strip and
    (iii) metering means for distributing the sample from the through hole along a predetermined path to each of the assay areas and
  (b) determining the analyte concentration by observing the assay area that changes color and that is most distant from the first end of the strip.

* * * * *